United States Patent
Barrus

(10) Patent No.: US 10,722,271 B2
(45) Date of Patent: Jul. 28, 2020

(54) SPINAL FIXATION DEVICE

(71) Applicant: K2M, Inc., Leesburg, VA (US)

(72) Inventor: Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 16/172,084

(22) Filed: Oct. 26, 2018

(65) Prior Publication Data

US 2019/0059951 A1    Feb. 28, 2019

Related U.S. Application Data

(62) Division of application No. 14/185,193, filed on Feb. 20, 2014, now abandoned.

(51) Int. Cl.
*A61B 17/70* (2006.01)

(52) U.S. Cl.
CPC ........ *A61B 17/7032* (2013.01); *A61B 17/705* (2013.01); *A61B 17/7056* (2013.01)

(58) Field of Classification Search
CPC ............ A61B 17/7034; A61B 17/7035; A61B 17/7032; A61B 17/8685
See application file for complete search history.

(56) References Cited

U.S. PATENT DOCUMENTS

| | | |
|---|---|---|
| 5,005,562 A | 4/1991 | Cotrel |
| 5,257,993 A | 11/1993 | Asher et al. |
| 5,263,954 A | 11/1993 | Schlapfer et al. |
| 5,346,493 A | 9/1994 | Stahurski et al. |
| 5,368,594 A | 11/1994 | Martin et al. |
| 5,374,267 A | 12/1994 | Siegal |
| 5,379,363 A | 1/1995 | Bonicel et al. |
| 5,415,659 A | 5/1995 | Lee et al. |
| 5,437,669 A | 8/1995 | Yuan et al. |
| 5,476,464 A | 12/1995 | Metz-Stavenhagen et al. |
| 5,527,314 A | 6/1996 | Brumfield et al. |
| 5,542,946 A | 8/1996 | Logroscino et al. |
| 5,575,792 A | 11/1996 | Errico et al. |

(Continued)

FOREIGN PATENT DOCUMENTS

| | | |
|---|---|---|
| WO | 96021396 A1 | 7/1996 |
| WO | 2009091689 A1 | 7/2009 |

(Continued)

OTHER PUBLICATIONS

Australian Examination Report for AU2015200634 of Nov. 19, 2018.
Extended European Search Report for EP 15155219.7 dated Jul. 9, 2015.

*Primary Examiner* — Julianna N Harvey
(74) *Attorney, Agent, or Firm* — Lerner, David, Littenberg, Krumholz & Mentlik, LLP

(57) ABSTRACT

A spinal fixation device is provided. The spinal fixation device includes a body portion including a stud portion defining a first annular groove. An outer housing is positionable on the stud portion of the body portion. An inner housing defines a second annular groove and is positionable between the outer housing and the stud portion. A ring member is positionable within each of the first and second annular grooves of the respective stud portion and inner housing to lock the inner housing to the body portion and to fixedly couple the outer housing to the stud portion.

20 Claims, 10 Drawing Sheets

(56) References Cited

U.S. PATENT DOCUMENTS

| | | |
|---|---|---|
| 5,578,033 A | 11/1996 | Errico et al. |
| 5,584,832 A | 12/1996 | Schlapfer |
| 5,609,592 A | 3/1997 | Brumfield et al. |
| 5,609,593 A | 3/1997 | Errico et al. |
| 5,609,594 A | 3/1997 | Errico et al. |
| 5,620,444 A | 4/1997 | Assaker |
| 5,630,816 A | 5/1997 | Kambin |
| 5,630,817 A | 5/1997 | Rokegem et al. |
| 5,667,506 A | 9/1997 | Sutterlin |
| 5,676,665 A | 10/1997 | Bryan |
| 5,688,273 A | 11/1997 | Errico et al. |
| 5,688,274 A | 11/1997 | Errico et al. |
| 5,725,527 A | 3/1998 | Biedermann et al. |
| 5,733,285 A | 3/1998 | Errico et al. |
| 5,741,254 A | 4/1998 | Henry et al. |
| 5,782,957 A | 7/1998 | Rinker et al. |
| 5,810,816 A | 9/1998 | Roussouly et al. |
| 5,810,817 A | 9/1998 | Roussouly et al. |
| 5,810,818 A | 9/1998 | Errico et al. |
| 5,888,221 A | 3/1999 | Gelbard |
| 5,928,232 A | 7/1999 | Howland et al. |
| 5,989,250 A | 11/1999 | Wagner et al. |
| 6,010,503 A | 1/2000 | Richelsoph et al. |
| 6,077,263 A | 6/2000 | Ameil et al. |
| 6,086,588 A | 7/2000 | Ameil et al. |
| 6,132,430 A | 10/2000 | Wagner |
| 6,322,562 B1 | 11/2001 | Wolter |
| 6,352,537 B1 | 3/2002 | Strnad |
| 6,416,515 B1 | 7/2002 | Wagner |
| 6,475,218 B2 | 11/2002 | Goumay et al. |
| 6,485,491 B1 | 11/2002 | Farris et al. |
| 6,554,831 B1 | 4/2003 | Rivard et al. |
| 6,562,040 B1 | 5/2003 | Wagner |
| 6,565,565 B1 | 5/2003 | Yuan et al. |
| 6,589,243 B1 | 7/2003 | Viart et al. |
| 6,595,992 B1 | 7/2003 | Wagner et al. |
| 6,613,050 B1 | 9/2003 | Wagner et al. |
| 6,626,908 B2 | 9/2003 | Cooper et al. |
| 6,641,585 B2 | 11/2003 | Sato et al. |
| 6,656,180 B2 | 12/2003 | Stahurski |
| 6,740,089 B2 | 5/2004 | Haider |
| 6,746,449 B2 | 6/2004 | Jones et al. |
| 6,749,361 B2 | 6/2004 | Hermann et al. |
| 6,911,030 B1 | 6/2005 | Vanacker et al. |
| 6,945,972 B2 | 9/2005 | Frigg |
| RE39,035 E | 3/2006 | Finn et al. |
| 7,160,300 B2 | 1/2007 | Jackson |
| 7,332,979 B2 | 2/2008 | Connell et al. |
| 7,338,490 B2 | 3/2008 | Ogilvie et al. |
| 7,485,133 B2 | 2/2009 | Cannon et al. |
| 7,608,095 B2 | 10/2009 | Yuan et al. |
| 7,651,516 B2 | 1/2010 | Petit et al. |
| 7,674,277 B2 | 3/2010 | Burd et al. |
| 7,780,703 B2 | 8/2010 | Yuan et al. |
| 7,785,352 B2 | 8/2010 | Snyder et al. |
| 7,789,899 B2 | 9/2010 | Markworth et al. |
| 7,819,901 B2 | 10/2010 | Yuan et al. |
| 7,935,133 B2 | 5/2011 | Malek |
| 7,988,694 B2 | 8/2011 | Barrus et al. |
| 8,814,919 B2 | 8/2014 | Barrus et al. |
| 2004/0220570 A1 | 11/2004 | Frigg |
| 2005/0113927 A1* | 5/2005 | Malek .............. A61B 17/7008 623/17.16 |
| 2006/0084990 A1 | 4/2006 | Goumay et al. |
| 2007/0016189 A1 | 1/2007 | Lake |
| 2007/0093817 A1* | 4/2007 | Barrus .............. A61B 17/7032 606/264 |
| 2007/0213732 A1 | 9/2007 | Khanna et al. |
| 2008/0132957 A1* | 6/2008 | Matthis ............. A61B 17/7032 606/301 |
| 2009/0318970 A1 | 12/2009 | Butler et al. |
| 2010/0222822 A1 | 9/2010 | Farris et al. |
| 2010/0274291 A1 | 10/2010 | McClellan, III et al. |
| 2010/0305616 A1 | 12/2010 | Carbone |

FOREIGN PATENT DOCUMENTS

| | | |
|---|---|---|
| WO | 2011057227 A1 | 5/2011 |
| WO | 2012030712 A1 | 3/2012 |

* cited by examiner

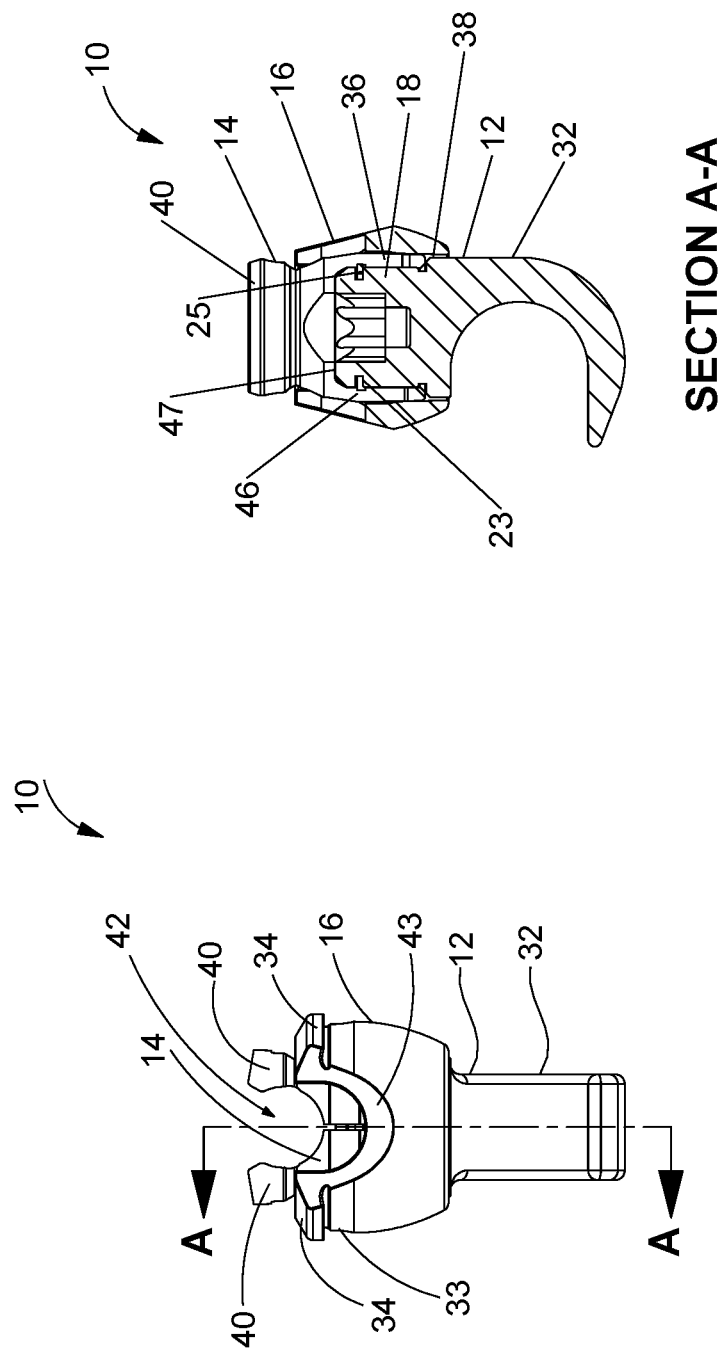

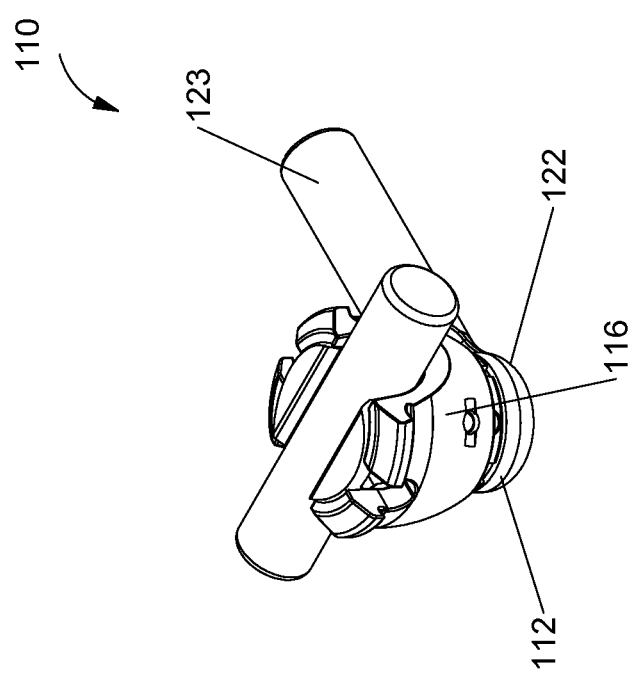

SPINAL FIXATION DEVICE

CROSS REFERENCE TO RELATED APPLICATIONS

This application is a divisional of U.S. patent application Ser. No. 14/185,193, filed on Feb. 20, 2014, the entire content of which is hereby incorporated by reference herein.

BACKGROUND

Technical Field

The present disclosure relates to spinal fixation devices. More particularly, the present disclosure relates to spinal fixation devices that are connectable to spinal rods used in spinal constructs.

Description of Related Art

There are many known spinal conditions, e.g., scoliosis, that require the imposition and/or maintenance of corrective forces on the spine in order to return the spine to its normal condition. As a result, numerous devices (e.g., alignment systems) have been developed for use in spinal fixation. One type of spinal construct may include, for example, one or more spinal rods that can be placed parallel to the spine with fixation devices (such as hooks, screws, or plates) interconnected between the spinal rods and selected portions of the spine. The spinal rods can be connected to each other via cross-connecting members to provide a more rigid support and alignment system.

Usually, the surgeon attaches the spinal fixation devices to the spine in appropriate anatomical positions and then attaches the spinal rod to the fixation devices. In conjunction, the surgeon manipulates the spinal column and/or individual vertebra to provide the desired treatment for the spinal defect. Subsequently, the spinal rod and fixation devices are locked in a desired arrangement.

While the aforementioned spinal fixation devices are suitable for the above uses, there may exist a need for spinal fixation devices that are inexpensive to manufacture and easy to use.

SUMMARY

As can be appreciated, spinal fixation devices that are connectable to spinal rods used in spinal constructs may prove useful in the surgical arena.

An aspect of the present disclosure provides a spinal fixation device. The spinal fixation device includes a body portion including a stud portion defining a first annular groove. An outer housing is positionable on the stud portion. An inner housing defines a second annular groove and is positionable between the outer housing and the stud portion. A ring member is positionable within each of the first and second annular grooves of the respective stud portion and inner housing to lock the inner housing to the body portion and to fixedly couple the outer housing to the stud portion.

The stud portion of the body portion may include a cylindrical configuration. The inner housing may include a bore having a cylindrical configuration, which is configured to at least partially cover the stud portion when the inner housing is positioned through a bore of the outer housing.

The stud portion defines at least one opening that is alignable with an opening defined through the inner housing and an opening defined through the outer housing when the inner housing is positioned through the outer housing and on the stud portion. A pin is receivable within the openings of the stud portion, the inner housing and the outer housing to prevent rotation of the inner housing with respect to the outer housing and body portion. The bore and opening defined through the outer housing may be oriented perpendicular with respect to one another.

The inner housing may include two upright arms that are spaced-apart from one another to form a slot configured to receive a spinal rod. The two upright arms may be flexible and releasably connect the spinal rod within the slot. The inner and outer housing may assume a first, unlocked position in which the upright arms are permitted to flex to receive a spinal rod, and a second, locked position in which the inner and outer housings are taper locked so that the upright arms grip the rod to secure the rod to the spinal fixation device. Top surfaces of the inner and outer housings may be substantially co-planar The body portion may include a bottom portion having a hook configuration that is configured to engage a lamina of a vertebra of a patient. Alternatively, the body portion includes a bottom portion having an elongated configuration that is configured to connect to at least one other spinal fixation device.

The ring member may be flexible and include a C-shaped configuration, which allows the ring member to flex, thereby allowing the ring member to expand for attachment to the stud portion.

The ring member may have an inner diameter that may be slightly less than an outer diameter of the stud portion of the body portion. The ring member may have an outer diameter that is slightly greater than an inner diameter of the interior of the inner housing such that the ring member is receivable within both the first annular groove of the stud portion and the second annular groove of the inner housing to lock the inner housing to the body portion.

An aspect of the present disclosure provides a method for assembling a spinal fixation device. The spinal fixation device includes a body portion, an inner housing, an outer housing, and a ring member. Initially, the ring member is positioned in a first annular groove of a stud portion of the body portion of the spinal fixation device. The outer housing is positioned over the stud portion. Thereafter, the inner housing is positioned on the stud portion to engage the ring member with a second annular groove defined on the inner housing to lock the inner housing to the stud portion and to fixedly couple the outer housing to the stud portion of the body portion.

Positioning the inner housing on the stud portion to engage the ring member with the second annular groove may further include moving a distal end of the inner housing distally past the first annular groove until the ring member is received within the second annular groove.

Another aspect of the present disclosure provides a method for connecting a spinal rod to a spine of a patient. A spinal fixation device is provided and is configured to removably couple to the spinal rod. The spinal fixation device includes a body portion including a stud portion defining a first annular groove. An outer housing is positionable on the stud portion of the body portion. An inner housing defines a second annular groove and is positionable between the outer housing and the stud portion. A ring member is positionable within each of the first and second annular grooves of the respective stud portion and inner housing to lock the inner housing to the body portion and to fixedly couple the outer housing to the stud portion of the body portion. A ring member is seated within each of the first and second annular grooves of the respective stud portion and inner housing to lock the inner housing to the body portion. A spinal rod is, initially, positioned within a slot of the inner housing. The outer housing is then moved proximally relative to the inner housing to secure the spinal rod to the spinal fixation device. Thereafter, the bottom portion of the body portion is engaged with a lamina of a vertebra of the patient to secure the spinal rod to the spine of the patient.

Engaging the bottom portion of the body portion with the lamina of the vertebra of the patient may further include engaging a hook configuration of the bottom portion of the body portion with the lamina of the vertebra of a patient.

At least a second spinal fixation device may be connected to the spinal rod. An elongated configuration of a bottom portion of a body portion of the at least second spinal fixation device may be connected to at least a third spinal fixation device.

BRIEF DESCRIPTION OF THE DRAWINGS

Various embodiments of the present disclosure are described hereinbelow with references to the drawings, wherein:

FIG. 1 is a front view of a spinal hook in accordance with an embodiment of the present disclosure;

FIG. 2 is a cross-sectional view taken along line A-A of FIG. 1;

FIG. 11 is a side view of the spinal hook shown in FIG. 10 with the spinal rod in a locked state.

DETAILED DESCRIPTION

Figure 3:
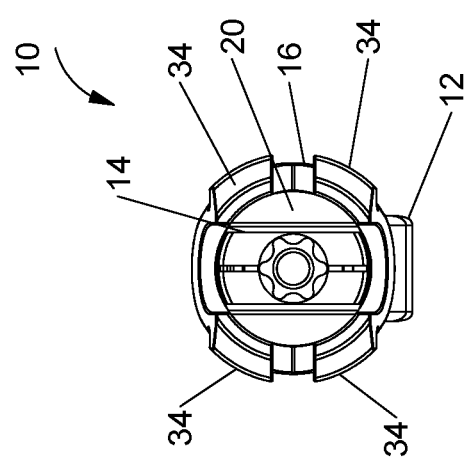
FIG. 3 is a top plan view of the spinal hook shown in FIG. 1.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the present disclosure are described in detail with reference to the drawing figures wherein like reference numerals identify similar or identical elements. As used herein, the term "distal" refers to a bottom portion of the spinal fixation device, while the term "proximal" refers to a top portion of the spinal fixation device, as shown in FIG. 1.

As described above, spinal fixation devices that are connectable to spinal rods used in spinal constructs may prove useful in the surgical arena, and such a spinal fixation device is described herein.

FIGS. 1 and 2 illustrate a spinal fixation device 10 according to an embodiment of the present disclosure. The spinal fixation device 10 includes a body portion 12 to which an inner housing 14 and an outer housing 16 connect. A taper lock is defined between the inner and outer housings such that in a first position the spinal fixation is unlocked and able to receive a rod, and in a second position the taper lock between the inner and outer housings compresses the spinal fixation device against the rod to secure the spinal fixation device to the rod. The spinal fixation device 10 may be formed from any suitable biocompatible metal (e.g., stainless steel, titanium, titanium alloys, cobalt chrome, etc.).

Figure 5:
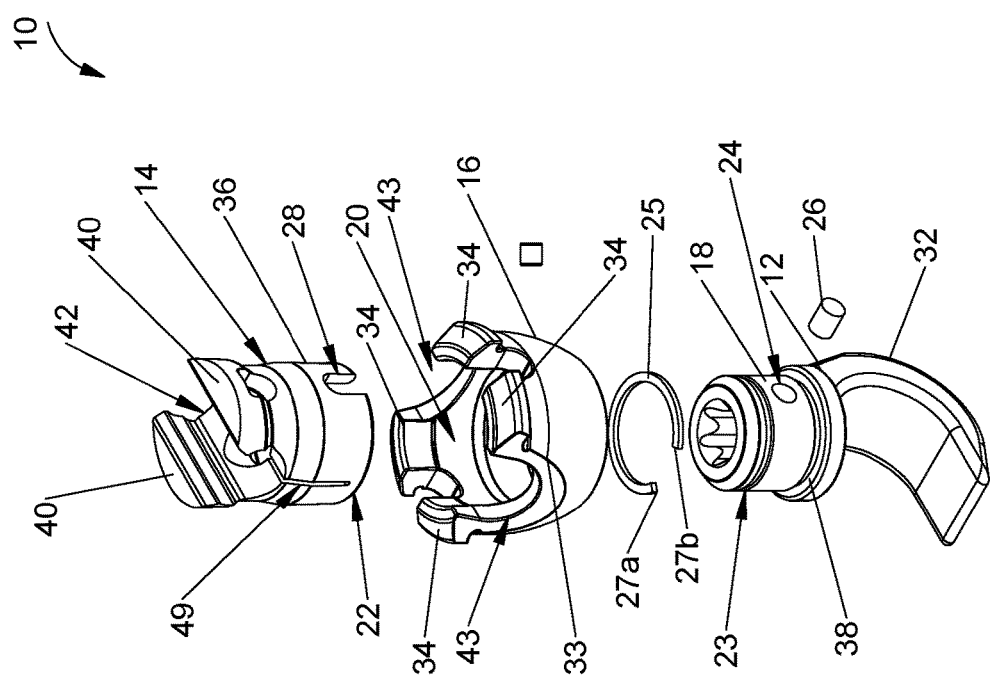
FIG. 5 is an exploded view of the spinal hook shown in FIG. 1 with parts separated.
Figure 6:
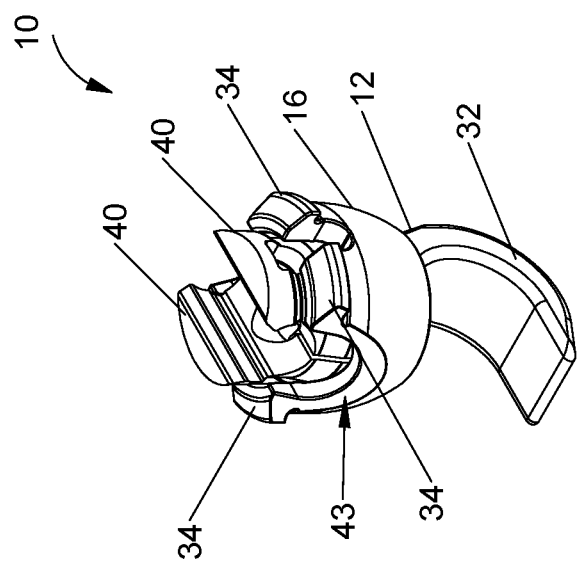
FIG. 6 is a perspective view of the spinal hook shown in FIG. 1.

Body portion 12 includes a stud portion 18 having a generally cylindrical configuration (see FIG. 5 for example). The stud portion 18 has a diameter that is less than a diameter of a bore 20 defined through the outer housing 16 (FIGS. 3 and 5) so that the outer housing 16 may be positioned on the stud portion 18. The diameter of the stud portion 18 is also less than a diameter of a bore 22 (FIG. 5) that is defined at least partially through the inner housing 14 so that the inner housing 14 may be positioned on the stud portion 18 between the stud portion 18 and the outer housing 16 (as best seen in FIG. 2). It is noted that in FIG. 2, the bore 22 defined in the inner housing 14 is not explicitly shown as the stud portion 18 is shown positioned within the bore 22.

An annular groove 23 (FIG. 2) is defined in a proximal portion of the stud portion 18 and is configured to receive a ring member 25 during manufacture of the spinal fixation device 10, as described in detail below. An outer diameter of the annular groove 23 is less than an outer diameter of the ring member 25 so that when the ring member 25 is seated within the annular groove 23, the ring member 25 extends out from the annular groove 23, the significance of which is described in detail below.

Figure 4:
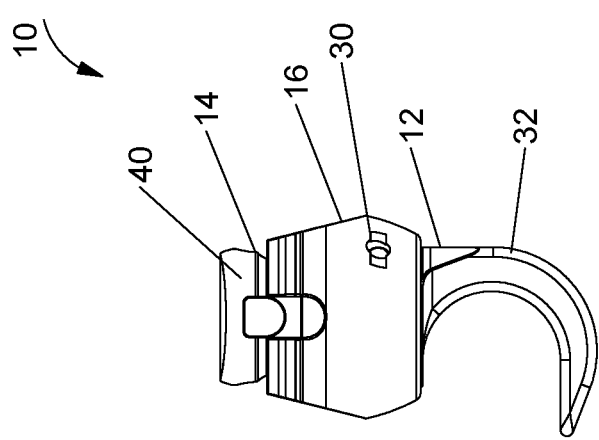
FIG. 4 is a side view of the spinal hook shown in FIG. 1 rotated 90°.

An opening 24 is defined through the stud portion 18 and is alignable with an opening 28 that is defined through the inner housing 14 and an opening 30 that is defined through the outer housing 16 (FIGS. 4 and 5). When aligned, the openings 24, 28, and 30 are configured to receive a pin 26 (FIG. 5), which, when received within the opening 24, 28, and 30, prevents rotation of the inner housing 14 with respect to the outer housing 16 and stud portion 18, and aligns the inner housing 14 with the outer housing 16 for maintaining a fixed relationship amongst these parts. In another embodiment, the pin 26 could also be removed to allow for movement of the rod locking portion (inner housing 14 and outer housing 16) with respect to the stud portion 18.

A bottom portion 32 of the body portion 12 includes a hook configuration that allows the body portion 12 to be engaged with a lamina of a vertebra of a patient. The hook configuration may include a tapered distal end, which may facilitate engaging the body portion 12 with the lamina of the patient. The bottom portion 32 may include other configurations, as will be described below.

The outer housing 16 includes a circumferential configuration and is positionable on the stud portion 18 of the body portion 12 (FIGS. 1-3 and 5). The outer housing 16 includes a tapered proximal end 33 including a plurality of fingers 34 (FIGS. 1 and 5) that are spaced apart along the proximal end 33. The fingers 34 define a pair of opposing U-shaped channels or slots 43 (FIG. 5) configured to receive a spinal rod 35, which may be coupled to the inner housing 14 prior to positioning the inner housing 14 through the bore 20 of the outer housing 16 (see FIGS. 7 and 8 for example). Fingers 34 also define an annular gripping flange at the proximal end of the outer housing to facilitate gripping of the outer housing by a locking instrument.

For a more detailed description of the outer housing 16, reference is made to U.S. patent application Ser. No. 12/739, 461, the entire contents of which are incorporated herein by reference.

The inner housing 14 includes a cylindrical configuration having a distal end 36 that is insertable through the bore 20 of the outer housing 16 (FIGS. 2 and 5). The distal end 36 is configured to rest on an annular flange or lip 38, which extends along the stud portion 18 of the body portion 12, when the inner housing 14 is locked to the body portion 12, (FIGS. 2 and 5). The lip 38 helps support the inner housing 14 when the inner housing 14 is locked to the body portion 12. The distal end 36 of the inner housing 14 defines the bore 22, which is configured to receive the stud portion 18 of the body portion 12 so that the inner housing 14 and body portion 12 can be locked together.

The inner housing 14 includes two upright arms 40 that are spaced-apart from one another to form a u-shaped slot 42 that is alignable with the pair of slots 43 on the outer housing 16 to receive the spinal rod 35 (FIGS. 1, 5, and 7) when the inner housing 14 is coupled to the outer housing 16. The two upright arms 40 are relatively flexible and releasably connect the spinal rod 35 within the slot 42. Specifically, the dimensions of the slot 42 vary according to the flexure of the upright arms 40. Accordingly, as the upright arms 40 are moved closer to each other, the slot 42 decreases in size and when the upright arms 40 are moved away from each other, the slot 42 increases in size. Allowing the slot 42 to vary in size permits the inner housing 14 to accommodate spinal rods having differing outside diameters. Alternatively, compressing the upright arms 40 towards each other increasingly engages the outer surface of a surgical rod located in the slot 42, thereby frictionally securing the spinal rod in a desired position.

Figure 7:
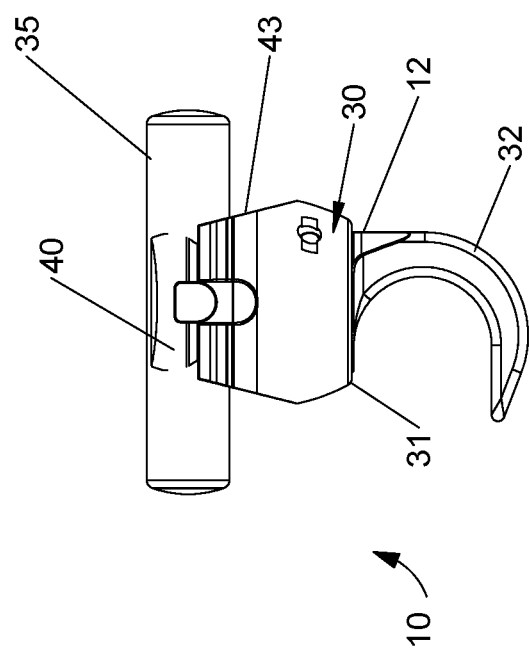
FIG. 7 is a side view of the spinal hook shown in FIG. 1 with a spinal rod positioned in a slot of an inner housing in an unlocked state.
Figure 8:
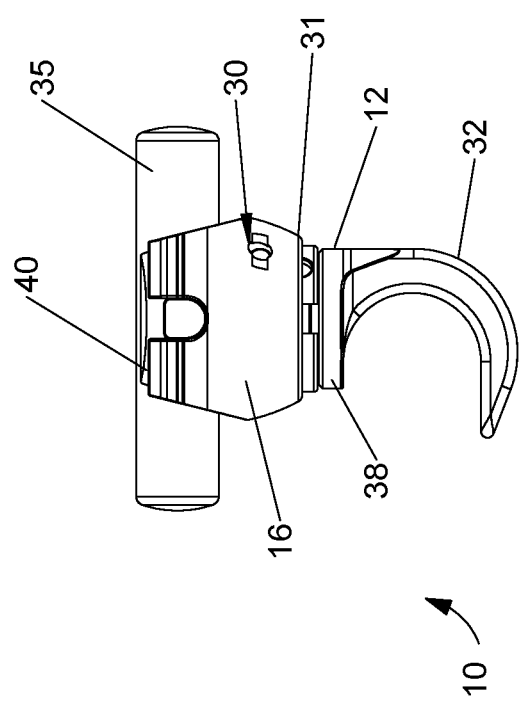
FIG. 8 is a side view of the spinal hook shown in FIG. 7 with the spinal rod in a locked state.

In embodiments, the inner and outer housings 14, 16, respectively, may assume a first, unlocked position in which the upright arms 40 are permitted to flex to receive a spinal rod (FIG. 7), and a second, locked position in which the inner and outer housings 14, 16 are taper locked so that the upright arms grip the rod to secure the rod to the spinal fixation device (FIG. 8).

The inner housing 14 includes an annular groove 46 that is defined along an interior wall 47 of the inner housing. In the illustrated embodiment, the annular groove 46 is disposed at a proximal end of the interior wall 47. The annular groove 46 is configured to receive at least a portion of the ring member 25 therein to lock the inner housing 14 to the body portion 12, as described in detail below.

Referring to FIG. 5, the ring member 25 may be formed from any suitable material, e.g., the metals described above. The ring member 25 includes an inner diameter that is slightly less than an outer diameter of the stud portion 18 of the body portion 12 and an outer diameter that is slightly greater than an inner diameter of the interior of the inner housing 14. This configuration of the ring member 25 allows the ring member 25 to be received within both the annular groove 23 of the stud portion 18 and the annular groove 46 of the inner housing 14 to lock the inner housing 14 to the body portion 12.

In the illustrated embodiment, the ring member 25 has a C-shaped configuration, which allows the ring member 25 to flex or open, thereby allowing the ring member 25 to expand for attachment to the stud portion 18 during assembly of the spinal fixation device 10. Specifically, opposing ends 27a, 27b (FIG. 5) of the ring member 25 are configured to flex or move away from one another thereby allowing the ring member 25 to be slid or pressed into position within the annular groove 23 of the stud portion 18. In embodiments, the ring member 25 can be replaced with a split ring (not explicitly shown).

To assemble the spinal fixation device 10, first, the ring member 25 is positioned within the annular groove 23 on the stud portion 18 of the body portion 12. In embodiments, this can be accomplished by pressing or pushing the opposing ends 27a, 27b against an annular wall portion (not explicitly shown) that defines the annular groove 23 causing the opposing ends 27a, 27b to move away from one another and allowing the ring member 25 to be press-fit into position within the annular groove 23. Next, the outer housing 16 can then be positioned over the ring member 25 and along the stud portion 18 of the body portion 12.

The inner housing 14 is then inserted into the bore 20 of the outer housing 16 to position the stud portion 18 into the bore 22 of the inner housing 14. The inner housing 14 is pushed distally along an exterior of the stud portion 18. The force used to push the distal end 36 distally along the stud portion 18 overcomes the frictional force of the ring member 25 against the interior wall 47 of the inner housing 14 and allows the inner housing 14 to be pushed distally along the stud portion 18. In embodiments, as the distal end 36 is being moved distally along the stud portion 18, the opposing ends 27a, 27b may move toward each other within the annular groove 23. Once the distal end 36 of the inner housing 14 reaches the flange 38 of the stud portion 18, the annular groove 46 of the inner housing 14 will be aligned with the annular groove 23 of the stud portion 18 and the ring member 25 will spring into engagement with the annular groove 46, which, in turn, locks the inner housing 14 to the body portion 12.

In the assembled configuration, the spinal fixation device 10 can be utilized to secure a spinal rod to a spine of the patient. Specifically, referring to FIGS. 7 and 8, in the assembled configuration, a distal end 31 of the outer housing 16 is positioned distal of (or below) the flange 38 of the stud portion 18. With the outer housing 16 in this configuration, the spinal rod 35 may be positioned within the slot 42 of the inner housing 14 between the upright arms 40, which will engage the spinal rod 35 to maintain the spinal rod 35 in a substantially fixed configuration (FIG. 7).

Thereafter, the outer housing 16 is moved proximally to align the plurality of fingers 34 of the outer housing 16 with the upright arms 40 of the inner housing 14 (FIG. 8). In this aligned configuration, the tapered proximal end 33 of the outer housing 16 causes an interior surface of the plurality of fingers 34 to compress the upright arms 40 against the spinal rod 35 to secure the spinal rod 35 to the spinal fixation device 10. The annular gripping flange defined by fingers 34 advantageously permits a locking instrument to engage the proximal portion of the outer housing 16 to move the outer housing 16 proximally relative to the inner housing 14 without abutting bone. As shown in FIG. 8, in the locked position the top surfaces of the inner and outer housings 14, 16, respectively, and the rod are substantially co-planer and present a low profile above the bone engaged by the hook.

Thereafter, the hook configuration of the bottom portion 32 of the body portion 12 is engaged with a lamina of a vertebra of the patient to secure the spinal rod 35 to the spine of the patient. To release the spinal rod 35 from between the upright arms 40 of the inner housing 14, a user simply pushes the outer housing 16 distally in relation to the inner housing 14 to return the outer housing 16 to its initial assembled configuration, i.e., the distal end 31 will again be positioned distal of the flange 38 of the stud portion 18 (FIG. 7). The spinal rod 35 can then be removed from within the slot 42 of the inner housing 14. An example of a suitable locking device and an unlocking device is disclosed in U.S. Pat. No. 7,988,694, the entire contents of which are hereby incorporated by reference herein.

Figure 9:
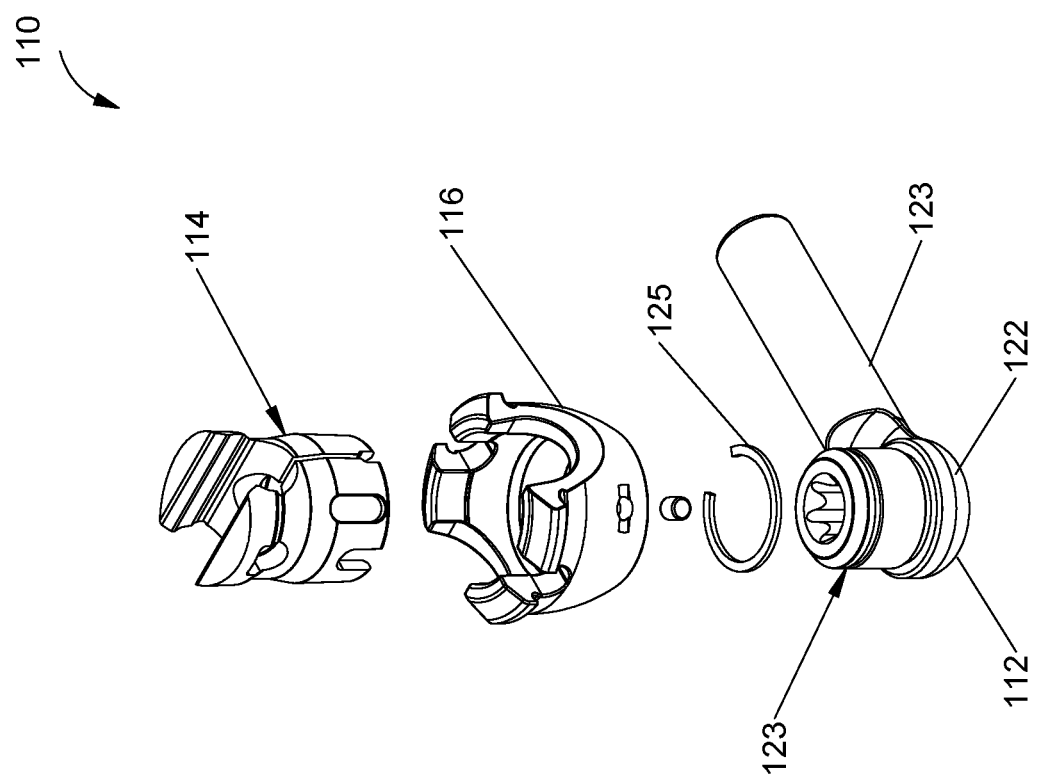
FIG. 9 is an exploded view of a spinal fixation device with parts separated according to another embodiment of the present disclosure.
Figure 10:
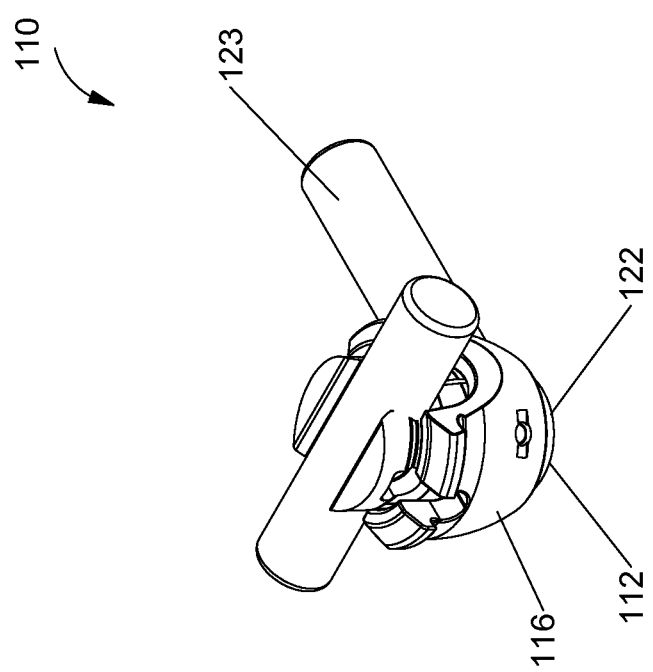
FIG. 10 is a side view of the spinal fixation device shown in FIG. 9 with a spinal rod positioned in a slot of an inner housing in an unlocked state.

From the foregoing and with reference to the various figure drawings, those skilled in the art will appreciate that certain modifications can also be made to the present disclosure without departing from the scope of the same. For example, while the bottom portion 22 of the body portion 12 has been described herein as including a hook configuration, the bottom portion 22 may be provided with other configurations. For example, FIGS. 9-11 illustrate a spinal fixation device 110 according to another embodiment. The spinal fixation device 110 is substantially identical to the spinal fixation device 10 and includes the body portion 112, the inner housing 114, the outer housing 116 and the ring 125. Unlike the bottom portion 22, however, the bottom portion 122 of the body portion 112 is in the form of an elongated rod 123, which may be utilized to connect to another spinal fixation device 10, 110. Other than the bottom portion 122, the spinal fixation device 110 is identical to the spinal fixation device 10 and, therefore is not described in further detail.

The foregoing spinal fixation devices 10, 110 are easy to use and provide flexibility for a surgeon to generate/create various spinal constructs and, therefore may prove useful in the surgical arena.

In embodiments, the annular groove 23 of the stud portion 18 can be defined along a distal end of the stud portion 18. In this embodiment, the annular groove 46 of the inner housing 14 can be defined along a distal end of the interior wall 47, e.g., adjacent the distal end 36 of the inner housing 14.

In embodiments, an optional slit 49 (see FIG. 5 for example) can be defined through the inner housing 14 between the upright arms 40 to increase the flexibility of the upright arms 40 to accommodate spinal rods having differing outside diameters.

While several embodiments of the disclosure have been shown in the drawings, it is not intended that the disclosure be limited thereto, as it is intended that the disclosure be as broad in scope as the art will allow and that the specification be read likewise. For example, other configurations of the body portion are contemplated. It also is contemplated that the inner and outer housing assembly with the ring therebetween may be used to assemble a taper lock head to a screw, especially to accommodate a screw head which is too large to enter through the bottom of the outer housing. Therefore, the above description should not be construed as limiting, but merely as exemplifications of particular embodiments. Those skilled in the art will envision other modifications within the scope and spirit of the claims appended hereto.

What is claimed is:

1. A method for coupling a spinal rod, comprising:
coupling a first spinal fixation device to a vertebra, the first spinal fixation device including:
   a body portion including a stud portion defining a first annular groove and at least one opening, the body portion including a bottom portion defining a hook configuration;
   an outer housing having a bore and an opening defined through the outer housing transverse to the bore, the outer housing positionable on the stud portion;
   an inner housing defining a second annular groove and an opening therein, the inner housing positionable in a received position extending through the bore of the outer housing with the inner housing being between the outer housing and the stud portion, wherein, in the received position, the inner housing receives the stud so as to constrain movement between the body portion and the inner housing to rotation about a single axis, and the at least one opening of the stud portion is alignable with the opening defined in the inner housing and the opening defined through the outer housing; and
   a ring member positionable within each of the first and second annular grooves to lock the inner housing to the body portion and to fixedly couple the outer housing to the stud portion;
positioning a spinal rod within a slot of the inner housing;
moving the outer housing away from the bottom portion and relative to the inner housing to secure the spinal rod to the spinal fixation device; and
engaging the bottom portion with a portion of a vertebra to couple the spinal rod to a spine of a patient.

2. The method according to claim 1, including connecting at least a second spinal fixation device to the spinal rod.

3. The method according to claim 2, including connecting an elongated configuration of a bottom portion of a body portion of the at least second spinal fixation device to at least a third spinal fixation device.

4. The method according to claim 1, wherein coupling the first spinal fixation device to a vertebra includes the inner housing of the first spinal fixation device having arms extending therefrom.

5. The method according to claim 4, wherein coupling the first spinal fixation device to a vertebra includes the arms of the inner housing defining a U-shaped slot configured to releasably receive the spinal rod.

6. The method according to claim 5, wherein coupling the first spinal fixation device to a vertebra includes the outer housing being repositionable with respect to the inner housing between a first, unlocked position where the arms are permitted to flex to receive the spinal rod in the U-shaped slot and a second, locked position where the inner and outer housings are taper locked so that the arms are configured to grip the spinal rod disposed in the U-shaped slot.

7. The method according to claim 1, wherein coupling the first spinal fixation device to a vertebra includes the first spinal fixation device having a pin that is receivable within the openings of the stud portion, the inner housing, and the outer housing to prevent rotation of the inner housing with respect to the outer housing and body portion and align the inner housing with the outer housing for maintaining a fixed relationship between the inner housing and the outer housing.

8. The method according to claim 1, wherein coupling the first spinal fixation device to a vertebra includes the top surfaces of the inner and outer housing being substantially co-planar.

9. The method according to claim 1, wherein coupling the first spinal fixation device to a vertebra includes the ring member being flexible.

10. The method according to claim 9, wherein coupling the first spinal fixation device to a vertebra includes the ring member having a C-shaped configuration which allows the ring member to flex, thereby allowing the ring member to expand for attachment to the stud portion.

11. The method according to claim 1, wherein coupling the first spinal fixation device to a vertebra includes the ring member having an inner diameter that is slightly less than an outer diameter of the first annular groove of the stud portion.

12. The method according to claim 11, wherein coupling the first spinal fixation device to a vertebra includes the ring member having an outer diameter that is slightly greater than an inner diameter of an interior of the inner housing such that the ring member is receivable within both the first annular groove of the stud portion and the second annular groove of the inner housing to lock the inner housing to the body portion.

13. A method for coupling a spinal rod, comprising:
coupling a first spinal fixation device to a vertebra, the first spinal fixation device including:
a body portion including a stud portion defining a first annular groove and at least one opening, the body portion including a bottom portion defining a hook configuration;
an outer housing having a bore and an opening defined through the outer housing, the outer housing positionable on the stud portion;
an inner housing defining a second annular groove and an opening therein, the inner housing positionable in a received position extending through the bore of the outer housing with the inner housing being between the outer housing and the stud portion, wherein, in the received position, the inner housing receives the stud so as to constrain movement between the body portion and the inner housing to rotation about a single axis, and the at least one opening of the stud portion is alignable with the opening defined in the inner housing and the opening defined through the outer housing;
a ring member positionable within each of the first and second annular grooves to lock the inner housing to the body portion and to fixedly couple the outer housing to the stud portion; and
a pin receivable within the openings of the stud portion, the inner housing, and the outer housing to prevent rotation of the inner housing with respect to the outer housing and body portion and to align the inner housing with the outer housing for maintaining a fixed relationship between the inner housing and the outer housing;
positioning a spinal rod within a slot of the inner housing;
moving the outer housing away from the bottom portion and relative to the inner housing to secure the spinal rod to the spinal fixation device; and
engaging the bottom portion with a portion of a vertebra to couple the spinal rod to a spine of a patient.

14. The method according to claim 13, wherein coupling the first spinal fixation device to a vertebra includes the inner housing of the first spinal fixation device having arms extending therefrom, the arms of the inner housing defining a U-shaped slot configured to releasably receive the spinal rod, and wherein the outer housing is repositionable with respect to the inner housing between a first, unlocked position where the arms are permitted to flex to receive the spinal rod in the U-shaped slot and a second, locked position where the inner and outer housings are taper locked so that the arms are configured to grip the spinal rod disposed in the U-shaped slot.

15. The method according to claim 13, wherein coupling the first spinal fixation device to a vertebra includes the top surfaces of the inner and outer housing being substantially co-planar.

16. The method according to claim 13, wherein coupling the first spinal fixation device to a vertebra includes the ring member being flexible.

17. The method according to claim 16, wherein coupling the first spinal fixation device to a vertebra includes the ring member having a C-shaped configuration which allows the ring member to flex, thereby allowing the ring member to expand for attachment to the stud portion.

18. The method according to claim 13, wherein coupling the first spinal fixation device to a vertebra includes the ring member having an inner diameter that is slightly less than an outer diameter of the first annular groove of the stud portion.

19. The method according to claim 18, wherein coupling the first spinal fixation device to a vertebra includes the ring member having an outer diameter that is slightly greater than an inner diameter of an interior of the inner housing such that the ring member is receivable within both the first annular groove of the stud portion and the second annular groove of the inner housing to lock the inner housing to the body portion.

20. A method for coupling a spinal rod, comprising:
coupling a first spinal fixation device to a vertebra, the first spinal fixation device including:
a body portion including a stud portion defining a first annular groove, the body portion including a bottom portion defining a hook configuration;
an outer housing positionable on the stud portion;
an inner housing defining a second annular groove, the inner housing positionable between the outer housing and the stud portion; and
a ring member positionable within each of the first and second annular grooves to lock the inner housing to the body portion and to fixedly couple the outer housing to the stud portion;
positioning a spinal rod within a slot of the inner housing;
moving the outer housing away from the bottom portion and relative to the inner housing to secure the spinal rod to the spinal fixation device;
engaging the bottom portion with a portion of a vertebra to couple the spinal rod to a spine of a patient;
connecting at least a second spinal fixation device to the spinal rod; and
connecting an elongated configuration of a bottom portion of a body portion of the at least second spinal fixation device to at least a third spinal fixation device.

* * * * *